United States Patent [19]

Murib et al.

[11] Patent Number: 4,611,069

[45] Date of Patent: Sep. 9, 1986

[54] PROCESS FOR PREPARING GAMMA-CAPROLACTONE BY ISOMERIZATION OF EPSILON-CAPROLACTONE

[75] Inventors: Jawad H. Murib, Cincinnati; John H. Kahn, Wyoming, both of Ohio

[73] Assignee: National Distillers and Chemical Corporation, New York, N.Y.

[21] Appl. No.: 624,307

[22] Filed: Jun. 25, 1984

[51] Int. Cl.[4] ............................................ C07D 307/32
[52] U.S. Cl. .................................................. 549/326
[58] Field of Search ......................................... 549/326

[56] References Cited

U.S. PATENT DOCUMENTS 3,004,989 10/1961 Hasek et al. ......................... 549/326
3,786,069 1/1974 Aviron-Violet et al. ............ 549/326
3,944,572 3/1976 King et al. ........................... 549/326

OTHER PUBLICATIONS

Tan CA. 81-135925y.
Rylander, Organic Synthesis with Noble Metal Catalysts, Academic Press, 1973.

Primary Examiner—Jane T. Fan
Attorney, Agent, or Firm—Kenneth D. Tremain

[57] ABSTRACT

A process for preparing gamma-caprolactone comprising isomerizing epsilon-caprolactone in an aqueous medium in the presence of catalytically effective amounts of hydriodic acid or hydrobromic acid wherein the catalyst is optionally promoted with a Group VIII metal. The temperature for the reaction is in the range of about 175° C. to about 250° C. and the ratio of water to epsilon-caprolactone is at least about 1:1.

2 Claims, No Drawings

PROCESS FOR PREPARING GAMMA-CAPROLACTONE BY ISOMERIZATION OF EPSILON-CAPROLACTONE

FIELD OF THE INVENTION

This invention relates to a process for the manufacture of lactones and more particularly to a process for the manufacture of gamma-caprolactone.

BACKGROUND OF THE INVENTION

Gamma-caprolactone is commercially and industrially attractive because of its use as a flavor additive in foods and tobacco and for its potential as an intermediate for insecticides.

Gamma-caprolactone (γ-caprolactone) has the structure:

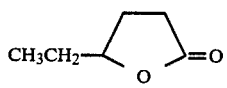

Gamma-caprolactone is also known as 4-hexalactone and 4-ethyl butyrolactone and in Chemical Abstracts, it is listed as 5-Ethyldihydro-2 (3H) furanone with a registry number of 695-06-7.

Various prior art methods exist for the production of gamma-caprolactone, but these methods are either expensive or do not produce good yields.

U.S. Pat. No. 3,944,572 to King, et al. discloses a process for the isomerization of epsilon-lactones to gammalactones. The process of King, et al. is a two-step process comprising heating epsilon-caprolactone in a vapor phase at a temperature of from 250° C. to 400° C. in the presence of an activated refractory oxide material catalyst such as activated alumina to produce hexenoic acid and 15–20% of gamma-caprolactone at the end of this first stage. The hexenoic acid which is a monounsaturated carboxylic acid is subjected to cyclising by contacting it with a catalyst comprising a strong protonating agent which may be a strong acid, a cation exchange resin in the free acid form, a strong acidic mixture containing hydrogen ions such as hydrogen halides and acetic acid or similar protonating substances.

Chemical Abstracts 76-59006d of Ger. Offen. No. 2,122,501 assigned to Rhone-Poulenc S.A. discloses the isomerization of epsilon-caprolactone in benzene in the presence of borophosphoric acid at 250° C. to produce gamma-caprolactone in relatively low yields.

"Isomerization of Epsilon-Caprolactone" by Tan, et al., Hokkaido Daigaku Kogakubu Kenkyu Hokoku, 70, pp. 115–119 (1974) abstracted in Chemical Abstracts 81-135925y discloses a process for the production of gamma-caprolactone by the isomerization of epsilon-caprolactone. According to Tan, et al., epsilon-caprolactone in an aqueous solution of ammonium chloride is heated at 300° C. to yield gamma-caprolactone and a small amount of delta-caprolactone. The epsilon-caprolactone isomerization can also be carried out in an aqueous solution of hydrochloric acid at 300° C. The reaction yielded approximately 40% of gamma and delta-caprolactones.

While the process described by Tan, et al. yields gamma-caprolactone in a one-step isomerization process, the process, however, disadvantageously requires a relatively high temperature, i.e., about 300° C., and yields gamma-caprolactone and a small amount of delta-caprolactone in only a 40% yield.

SUMMARY OF THE INVENTION

It is therefore an object of the present invention to provide a one-step process for the economical production of gamma-caprolactone in good yields utilizing relatively mild reaction conditions.

To achieve the objects in accordance with the purposes of the invention, as embodied and broadly described herein, the invention comprises a process for preparing gamma-caprolactone comprising isomerizing epsilon-caprolactone in the presence of catalytically effective amounts of hydriodic acid or hydrobromic acid in a solvent comprising water at a temperature in the range of from about 175° C. to about 250° C. Hydriodic acid is the preferred protonating catalyst. Optionally, the isomerization reaction may be promoted with a catalyst-promoting effective amount of a Group VIII metal.

DETAILED DESCRIPTION OF THE INVENTION

In accordance with the present invention, it has unexpectedly been found that gamma-caprolactone is prepared in superior yields by isomerizing epsilon-caprolactone in an aqueous medium in the presence of catalytically effective amounts of hydriodic acid or hydrobromic acid, which acids serve as protonating catalysts for the reaction.

For the purposes herein, catalytically effective amounts of the aqueous hydriodic or hydrobromic acid have been found to be, for example, in a mole ratio range of epsilon-caprolactone to hydriodic or hydrobromic acid of about 5:1 to about 60:1, respectively. This range can vary considerably and the amount of hydriodic or hydrobromic acid present may be outside this range and still produce gamma-caprolactone in accordance with the process of the invention although this mole ratio range of hydriodic or hydrobromic acid has been found to effectively produce superior yields of gamma-caprolactone. Moreover the mole ratio can be effected by the optional Group VIII metal promoter which may act to reduce the amount of hydriodic or hydrobromic acid required to act as an effective catalyst to produce the gamma-caprolactone in high yield.

The isomerization reaction of the present invention is carried out in an aqueous medium wherein the mole ratio of total water present to the epsilon-caprolactone starting material is at least about 1:1. Preferably the mole ratio of water to epsilon-caprolactone is from about 1:1 to about 10:1. The mole ratio of water to epsilon-caprolactone can vary considerably and may exceed the preferred range according to the process of the invention. Present knowledge indicates, however, that a mole ratio within the preferred range contributes to the production of superior yields of gamma-caprolactone.

The isomerization reaction is carried out in a temperature range of about 175° C. to about 250° C. Preferably the temperature range of the isomerization reaction is about 200° C. to about 225° C. and more preferably the temperature is about 200° C. The temperature of the reaction may vary greatly and even exceed the range specified above, although the ranges specified above have been found to produce superior yields of gamma-caprolactone. Generally, the reaction is carried out at atmospheric pressure but may be carried out under an increased pressure of an inert gas such as $CO_2$ or $N_2$.

The hydriodic or hydrobromic acid catalyst can optionally be promoted with a catalyst-promoting effective amount of a Group VIII metal (e.g., Ru, Pd, Pt, Ni, etc.) in accordance with the process of the invention. In those instances where an optional promoter is desired, the preferred catalyst promoter is ruthenium metal on a carbon support.

In accordance with the process of the invention, yields of up to 96% of gamma-caprolactone and a small amount of delta-caprolactone are obtainable. The percent yield of gamma-caprolactone will vary as the reaction conditions vary as will be illustrated by the examples which follow. The superior yields of gamma-caprolactone which are achieved according to the efficient process of the invention represent an improvement over those yields obtained by prior art isomerization processes utilizing hydrochloric acid or borophosphoric acid and this improvement is also illustrated in the example section which follows.

A reaction time of 6 hours has been found to be sufficient for producing high yields of gamma-caprolactone on the scale of reactions utilized in the present example hereinafter detailed. Reaction times may vary as quantities of reactants used and reaction conditions vary, as would be known to those skilled in the art. Thus, the following examples are not intended to be limiting of the scope of the present invention. In conjunction with the general and detailed description above, the examples provide further understanding of the present invention and outline further embodiments of the process of the invention.

The general scheme of reaction can be illustrated as follows:

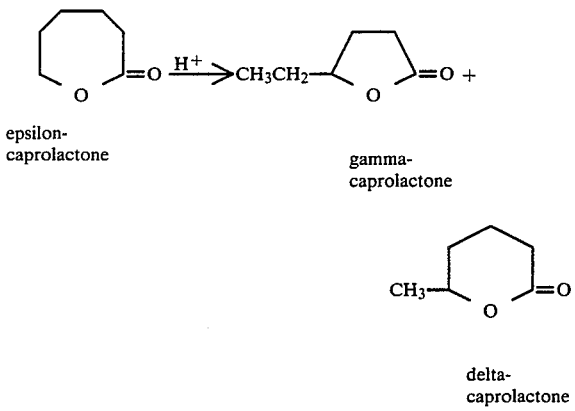

epsilon-caprolactone gamma-caprolactone delta-caprolactone

The starting materials, solvents, and reagents utilized in the examples whose method of preparation are not indicated, are commercially available compounds which would be available from chemical supply houses well known to the art.

EXAMPLE 1

A 71 ml Hastelloy pressure reactor with glass liner was charged with 5 ml (40 mM) epsilon-caprolactone, 5 ml (277 mM) water and 1 ml (6.5 mM) 57% aqueous hydriodic acid. The mixture was flushed with $N_2$ to displace any $O_2$, sealed and heated with shaking in an oven at 200° C. for six hours.

The reaction mixture contained 37 mM gamma-caprolactone which corresponds to a yield of 91% based on the starting amount of epsilon-caprolactone. The product solution was analyzed by gas chromatography and the presence of gamma-caprolactone was confirmed by mass and NMR spectra.

Separation of gamma-caprolactone from $H_2O$ to the extent of 97% was achieved by phase separation and chloroform extraction of the water layer.

EXAMPLE 2

The procedure of Example 1 was repeated except that the temperature was 225° C. The reaction mixture contained 16 mM gamma-caprolactone which corresponds to a yield of 40%.

EXAMPLE 3

The procedure of Example 1 was repeated except that the temperature was 175° C. The reaction mixture contained 7 mM gamma-caprolactone which corresponds to a yield of 17%.

EXAMPLE 4

The procedure of Example 1 was repeated except that the charge also contained 0.5 g 5% Ru/C. The reaction mixture contained 39 mM gamma-caprolactone which corresponds to a yield of 96%.

EXAMPLE 5

The procedure of Example 1 was repeated except that HBr was used as the catalyst. The reaction mixture contained 21 mM gamma-caprolactone which corresponds to a yield of 53%.

COMPARATIVE EXAMPLE 1

The procedure of Example 1 was repeated except that 1 ml of concentrated hydrochloric acid (12 mM) was used in place of hydriodic acid. The reaction mixture contained 7 mM gamma-caprolactone which corresponds to a yield of 17%.

As illustrated in Examples 1-5, the process of the invention provides for superior yields of gamma-caprolactone. The comparative example, utilizing hydrochloric acid as the protonating catalyst at a temperature of 200° C., produces gamma-caprolactone in yields inferior to those obtained under similar reaction conditions according to the process of the present invention.

The scope of the present invention is not limited by the description, examples, and suggestions used herein, and modifications can be made without departing from the spirit of the invention. Thus, it is intended that the present invention cover the modifications and variations of this invention provided they come within the scope of the appending claims and their equivalents.

What is claimed is:

1. A process for preparing gamma-caprolactone comprising isomerizing epsilon-caprolactone in an aqueous medium in the presence of a catalytically effective amount of hydriodic acid or hydrobromic acid with a catalyst-promoting effective amount of ruthenium metal on a carbon support, at a temperature in the range of about 200° C. to about 225° C., wherein the mole ratio of water to epsilon-caprolactone is in the range of about 1:1 to about 10:1.

2. A process for preparing gamma-caprolactone comprising isomerizing epsilon-caprolactone in an aqueous medium in the presence of a catalytically effective amount of hydriodic acid wherein the hydriodic acid catalyst is promoted with a catalyst-promoting effective amount of ruthenium metal on a carbon support, at a temperature of about 200° C., wherein the mole ratio of water to epsilon-caprolactone is in the range of about 1:1 to about 10:1.

* * * * *